United States Patent
Kim et al.

(10) Patent No.: US 12,318,360 B2
(45) Date of Patent: Jun. 3, 2025

(54) RIVASTIGMINE PATCH FOR LONG-TERM ADMINISTRATION

(71) Applicant: SK CHEMICALS CO., LTD., Seongnam-si (KR)

(72) Inventors: Namho Kim, Seongnam-si (KR); Wonjae Choi, Seongnam-si (KR); Hunseung Yoo, Seongnam-si (KR); Soo Min Lee, Seongnam-si (KR); Yeo-Jin Park, Seongnam-si (KR); Sung-Hyuk Kim, Seongnam-si (KR); Jong-su Yoo, Seongnam-si (KR); Young-me Lee, Seongnam-si (KR)

(73) Assignee: SK CHEMICALS CO., LTD., Seongnam-si (KR)

( * ) Notice: Subject to any disclaimer, the term of this patent is extended or adjusted under 35 U.S.C. 154(b) by 763 days.

(21) Appl. No.: 17/271,638

(22) PCT Filed: Aug. 30, 2019

(86) PCT No.: PCT/KR2019/011212
§ 371 (c)(1),
(2) Date: Feb. 26, 2021

(87) PCT Pub. No.: WO2020/046073
PCT Pub. Date: Mar. 5, 2020

(65) Prior Publication Data
US 2021/0330630 A1    Oct. 28, 2021

(30) Foreign Application Priority Data
Aug. 31, 2018    (KR) .................. 10-2018-0103849

(51) Int. Cl.
*A61K 31/27*    (2006.01)
*A61K 9/70*    (2006.01)
*A61K 47/02*    (2006.01)

(52) U.S. Cl.
CPC ............ *A61K 31/27* (2013.01); *A61K 9/7084* (2013.01); *A61K 47/02* (2013.01)

(58) Field of Classification Search
CPC ....... A61K 31/27; A61K 9/7084; A61K 47/02
See application file for complete search history.

(56) References Cited

U.S. PATENT DOCUMENTS 6,335,031 B1    1/2002    Asmussen et al.
8,864,727 B2    10/2014    Lee
(Continued)

FOREIGN PATENT DOCUMENTS

JP    03291218 A    12/1991
JP    2004502725 A    1/2004
(Continued)

OTHER PUBLICATIONS

International Search Report dated Dec. 26, 2019 for International Patent Application No. PCT/KR2019/011212, 11 pages with English translation.

*Primary Examiner* — Blessing M Fubara
(74) *Attorney, Agent, or Firm* — MH2 Technology Law Group, LLP (57) ABSTRACT

The present invention relates to a patch comprising a high content of rivastigmine per unit area, which can be continuously administered for a long time. The rivastigmine patch according to the present invention is capable of continuous release of rivastigmine for a long period of time, preferably 3 days, more preferably 4 days or more after attachment, and has excellent physical and chemical stability.

12 Claims, 3 Drawing Sheets

(56) References Cited

U.S. PATENT DOCUMENTS

| | | |
|---|---|---|
| 9,585,862 B2 | 3/2017 | Hwang et al. |
| 10,660,863 B2 | 5/2020 | Langer et al. |
| 2004/0086551 A1 | 5/2004 | Miller, II et al. |
| 2004/0086552 A1 | 5/2004 | Klokkers et al. |
| 2006/0292192 A1 | 12/2006 | Hasenzahl et al. |
| 2014/0220104 A1* | 8/2014 | Hwang ............... A61K 31/325 |
| | | 424/449 |
| 2015/0283097 A1* | 10/2015 | Murata ................. A61P 25/28 |
| | | 424/443 |
| 2017/0112781 A1* | 4/2017 | Shima ................. A61K 9/7084 |
| 2018/0028663 A1* | 2/2018 | Lee .................... A61K 31/445 |

FOREIGN PATENT DOCUMENTS

| | | |
|---|---|---|
| JP | 2006513160 A | 4/2006 |
| KR | 1020110030349 A | 3/2011 |
| KR | 101842309 B1 | 3/2018 |
| WO | 2014111790 A2 | 7/2014 |
| WO | 2016018858 A1 | 2/2016 |

\* cited by examiner

RIVASTIGMINE PATCH FOR LONG-TERM ADMINISTRATION

CROSS-REFERENCE TO RELATED APPLICATIONS

This application is a U.S. National Stage application of PCT/KR2019/011212 filed 30 Aug. 2019, which claims priority to Korean Patent Application No. 10-2018-0103849 filed 31 Aug. 2018, the entire disclosures of which are hereby incorporated by reference in their entireties.

TECHNICAL FIELD

The present invention relates to a patch comprising rivastigmine or a pharmaceutically acceptable salt thereof as an active ingredient, which can be continuously applied for a long period of time, preferably 3 days or more, more preferably 4 days or more.

BACKGROUND ART

Rivastigmine is used to treat or ameliorate Alzheimer's disease, etc., and inhibit acetylcholinesterase in the central nervous system. Such rivastigmine is commercially available as a patch formulation.

U.S. Pat. No. 6,335,031 relates to a transdermal composition containing rivastigmine or a salt thereof, and is characterized by using a stabilizer. Said invention discloses that it is difficult to secure a storage period necessary for commercial distribution since the transdermal composition containing rivastigmine is decomposed by oxidation reaction with oxygen even under closed storage conditions. In order to solve this problem, said invention discloses a composition for transdermal administration of rivastigmine wherein the composition comprises an antioxidant such as tocopherol, ascorbic acid, butylhydroxytoluene, butylhydroxyanisole, and propyl gallate.

To date, commercially available rivastigmine patches are only available for continuous administration over 24 hours. However, a patch that can be applied for a longer period of time is required for the convenience of the patient and the characteristics of the dementia patient to be treated. In order to release rivastigmine at an appropriate release rate over an extended time interval of more than 24 hours, long-term administration patches are bound to contain large amounts of rivastigmine, and due to this high content, a variety of problems, including cold flow problem arise.

That is, there is a need for a patch having good physical and chemical stability while releasing rivastigmine at an appropriate release rate for a long period of time even if it contains a high content of rivastigmine or a salt thereof.

DISCLOSURE

Technical Problem

Therefore, the problem to be solved by the present invention is to provide a patch which is physically stable and can release rivastigmine at an appropriate release rate for a long period of time and in which the stability of rivastigmine also are secured, even if the patch contains a high content of rivastigmine or a pharmaceutically acceptable salt thereof for long-term therapeutic application.

Technical Solution

In order to solve the above problem, the present disclosure provides a rivastigmine patch for transdermal treatment comprising (1) a backing film that serves to protect the patch and is inert to the components of the matrix, (2) a rivastigmine matrix layer that comprises rivastigmine or a pharmaceutically acceptable salt thereof, (3) a self-adhesive matrix layer that comprises an adhesive that adheres to the skin, and (4) a release liner to be removed before use, wherein the content per patch area of rivastigmine or a pharmaceutically acceptable salt thereof is 2 to 15 $mg/cm^2$, preferably 3.6 to 10.8 $mg/cm^2$, more preferably 5.4 to 9 $mg/cm^2$ based on the rivastigmine free base, and the rivastigmine matrix layer comprises hydrophobic silica.

In order to prepare a patch that is absorbed into the skin by releasing rivastigmine for a long period of time, preferably at least 2 days, more preferably 3 days or more, even more preferably 4 days or more, there is no choice but to increase the content of rivastigmine. For this reason, the height (thickness) of the rivastigmine matrix layer must exceed a certain level. In this case, the stability of the patch during storage or adhesion to the skin, particularly the stability of the layer comprising rivastigmine, became a problem, and the release rate of rivastigmine was also greatly affected.

While studying various means, the present inventors completed the present invention by confirming that physical and chemical stability can be secured through the same method as the present disclosure and that an appropriate release rate can be maintained even during long-term application.

The rivastigmine patch of the present disclosure comprises (1) a backing film, (2) a rivastigmine matrix layer comprising rivastigmine or a pharmaceutically acceptable salt thereof, (3) a self-adhesive matrix layer comprising an adhesive that adheres to the skin, and (4) a release liner, which will be described in detail below.

Rivastigmine Matrix Layer

In the present invention, the rivastigmine matrix layer has a content per patch area of rivastigmine or a pharmaceutically acceptable salt thereof of 2 to 15 $mg/cm^2$, preferably 3.6 to 10.8 $mg/cm^2$, more preferably 5.4 to 9 $mg/cm^2$ based on the rivastigmine free base, and the rivastigmine matrix layer comprises hydrophobic silica in order to achieve the above object.

The aforementioned physical and chemical stability can be ensured through hydrophobic silica. In addition, due to the characteristics of rivastigmine, it is mixed in the adhesive layer to provide adhesion, and when rivastigmine is lost through skin penetration, the adhesion force may be reduced. In this case, it is believed that hydrophobic silica used in the present invention compensate for the loss of adhesive force and prevent structural deformation between the backing film and other layers. However, the present invention is not limited to these theoretical ideas.

In the present invention, the hydrophobic silica includes hydrophobic fumed silica, hydrophobic colloidal silica, hydrophobic precipitated silica, and hydrophobic plasma polymer coated silica, and the like. Among these, hydrophobic fumed silica is most preferred in terms of low temperature cold flow, storage stability, attachment or adhesion between layers, and release rate.

These hydrophobic fumed silicas include AEROSIL® R 972, R 974, R 104, R 106, R 202, R208, R 805, R 812, R 812 S, R 816, R 7200, R 8200, R 9200, R 711, RY 50, NY 50, NY 50 L, RY 200, RY 200 S, RX 50, NAX 50, RX 200, RX 300, R 504, NX 90 S, NX 90 G, RY 300, REA 90, REA 200, RY 51, NA 50 Y, RA 200 HS, NA 50 H, RA 200 H, NA 130 K, NA 200 Y, NX 130, RY 200 L, R 709, R 976 S, R972 Pharma, CAB-O-SIL® CT-1111G, CT-1206, CT-1221, TG-308F, TG-3110, TG-3130, TG-3155F, TG-5110, TG-5115F, TG-5180, TG-5182, TG-5182F, TG-5185F, TG-6110G, TG-6120F, TG-709F, TG-7120, TG-7180, TG-810G, TG-811F, TG-815F, TG-818F, TG-820F, TG-828F, TG-5022, TS-530, TS-610, TS-612, TS-620, TS-622, TS-710, TS-720, TS-720D, TS-720J, ULTRA-BOND, TG-C110, TG-C243, TG-C390, TG-C413, TG-C6020N, TS-382, TS-500, and HDK® V15, N20, T30, H13L, H15, H20, H30, H2000, H17, H18, etc. AEROSIL® R 972 Pharma is very preferred in terms of the object of the present invention (hereinafter R 972 is the same as R 972 Pharma).

As the hydrophobic colloidal silica, AEROSIL® R 972 Pharma (silica dimethyl silylate) and the like are preferable.

As the hydrophobic precipitated silica, SIPERNAT® D 10, D 13, D 17, and the like are preferable. Plasma polymerized 1,7-octadiene (ppOD)-coated silica is preferable as the hydrophobic plasma polymer coated silica.

Preferably, the content of this hydrophobic silica is 10-30% by weight based on the total weight of the rivastigmine matrix layer.

Preferably, the rivastigmine matrix layer comprises 10-50% by weight of rivastigmine, 5-30% by weight of hydrophobic silica, and 30-80% by weight of an acrylic adhesive based on the total weight of the rivastigmine matrix layer. More preferably, the rivastigmine matrix layer comprises 20-40% by weight of rivastigmine, 10-20% by weight of hydrophobic silica, and 40-70% by weight of an acrylic adhesive based on the total weight of the rivastigmine matrix layer.

As the acrylic adhesive for forming the rivastigmine matrix layer, a copolymer of a (meth)acrylic acid ester monomer having an alkyl group of 1 to 12 carbon atoms and a polar monomer being copolymerizable with the (meth) acrylic acid ester monomer may be used. Examples of the (meth)acrylic acid ester monomer include butyl (meth) acrylate, hexyl (meth)acrylate, n-octyl (meth)acrylate, isooctyl (meth)acrylate, and 2-ethylhexyl (meth)acrylate, isononyl (meth)acrylate, and the like. In addition, examples of the polar monomer copolymerizable with the (meth) acrylic acid ester-based monomer include monomers containing carboxyl groups such as (meth)acrylic acid, maleic acid, and fumaric acid, and nitrogen-containing monomers like acrylamide, N-vinylpyrrolidone, and N-vinylcaprolactam. In the acrylic adhesive, the ratio of the (meth)acrylic acid ester monomer and the polar monomer is not particularly limited, but may generally have a weight ratio of 99 to 80:1 to 20. Examples of such acrylic adhesives include DURO-TAK™ 87-202A, 387-2510, 87-2510, 87-4287, 387-2287, 87-2287, 387-2516, 87-2516, 387-2525, 87-2525, 87-2979, 87-2074, 87-235A, 87-2353, 387-2353, 87-2852, 87-2051, 387-2051, 87-2052, 387-2052, 387-2054, 87-2054, 87-2677, 87-2194, 387-2196, 387-2825, 87-2825, 87-502A, 87-503A, 87-504A, 87-9088, 87-4098, and the like. Preferably, a random copolymer of 58-66 parts by weight of 2-ethylhexyl acrylate, 28-36 parts by weight of methyl acrylate, and 4-8 parts by weight of acrylic acid (e.g., Duro-Tak® 87-235A) can be used as the acrylic adhesive in terms of miscibility and compatibility.

The rivastigmine matrix layer of the present invention may further comprises an acrylic polymer like a copolymer of butyl methacrylate and methyl methacrylate (preferably, a copolymer having a weight average molecular weight of 130,000-170,000 g/mol, for example, PLASTOID™ B, EVONIK), methacrylic acid copolymer type A, B, C (preferably, methacrylic acid copolymer, type A, for example, Eudragit L100), and the like.

The rivastigmine matrix layer may further comprise an antioxidant to secure the chemical stability of rivastigmine or a pharmaceutically acceptable salt thereof, and such antioxidants, preferably, tocopherol, butylated hydroxyanisole (BHA), butylated hydroxytoluene (BHT) or a mixture thereof may be used. More preferably, tocopherol is used as an antioxidant in the patch of the present invention.

Self-Adhesive Matrix Layer

The rivastigmine patch of the present invention comprises a self-adhesive matrix layer in contact with skin, and a previously known skin adhesive layer may be used as the skin-contact self-adhesive matrix layer.

The self-adhesive matrix layer may comprise any one or more selected from an acrylic adhesive, a rubber-based adhesive, and a silicone-based adhesive as an adhesive polymer (adhesive).

As the acrylic adhesive, examples mentioned in the rivastigmine matrix layer may be used. As the silicone adhesive, preferably, dimethylsiloxane-treated trimethylated silica may be used. For example, DOW CORNING's BIO-PSA™ 7-4101, 7-4201, 7-4301, 7-4102, 7-4202, 7-4302, 7-4103, 7-4203, 7-4303, 7-4401, 7-4501, 7-4601, 7-4402, 7-4502, 7-4602, 7-4403, 7-4503, 7-4603, or mixtures thereof, may be used.

In the system of the present invention, it is preferable to use a mixture of two or more types of silicone adhesives having different physical properties as the silicone-based adhesive. Particularly, the mixture of BIO-PSA 7-4201 and 7-4301 (more preferably, a 1:1 weight ratio mixture) was more excellent in improving adhesion in patches comprising a large amount of rivastigmine.

As a rubber-based adhesive, for example, an adhesive formed by mixing a high-molecular and low-molecular polybutylene (PB) or poly isobutylene (PIB) may be used. Alternatively, an adhesive formed by mixing a styrene block copolymer-based styrene-isoprene-styrene (SIS) and polyisobutylene (PIB) may be used.

In this self-adhesive matrix layer, in order to aid in the stability of rivastigmine of the rivastigmine matrix layer in contact, the aforementioned antioxidant may be comprises.

In the self-adhesive matrix layer, an appropriate penetration enhancer may be further comprised in order to aid in the absorption of rivastigmine of the rivastigmine matrix layer in contact.

In addition, in the self-adhesive matrix layer, an appropriate adhesion enhancing agent may be further comprised in order to enhance the adhesion of the rivastigmine matrix layer in contact.

Release-Controlling Membrane

Preferably, the rivastigmine patch of the present invention may comprise a release-controlling membrane between the rivastigmine matrix layer and the self-adhesive matrix layer, and such release-controlling membrane is, for example, polypropylene membrane (e.g., Celgard™ 2400), polyethylene membrane (e.g., CoTran™ 9719 or 9720), or polyethylene membrane with a vinyl acetate ratio of 4.5-19% (e.g., CoTran™ 9707, 9702, 9728) can be used. The release-controlling membrane according to the present invention may have a porosity of up to 90% (e.g., Solupor™ 10P05A, Celgard™ 2400).

An ethylene vinyl acetate membrane is preferable as such a release-controlling membrane, and for example, 3M CoTran™ 9705, 9707, etc. may be preferably used as such an ethylene vinyl acetate membrane.

Typically, the release-controlling membrane has a thickness of 0.01 to 0.15 mm. The preferred thickness of the membrane is 0.025 to 0.080 mm Backing Film and Release Liner The backing film is blocked, i.e., distal. In a preferred embodiment, this backing film may be polyolefin, in particular polyethylene, or polyester as well as polyurethane. Further, preferably, a polyester foil such as polyethylene terephthalate foil can be used.

The release liner is a pull-off layer that is removed immediately before use. For example, polyurethane, polyvinyl acetate, polyvinylidene chloride, polypropylene, polycarbonate, polystyrene, polyethylene, polyethylene terephthalate, and polybutylene terephthalate may be used as the release liner. Alternatively, a paper surface-coated with the above polymer(s) may be used. Preferably, one-sided siliconized polymer foil is used.

Advantageous Effects

The present invention provides a rivastigmine patch that can be applied therapeutically for a long time by securing various aspects of physical and chemical stability, and releasing rivastigmine at a good rate for a long time, even if it comprises a high content of rivastigmine per unit area of the patch.

The rivastigmine patch of the present invention can freely control the release rate of rivastigmine by adjusting the release-controlling agent of the rivastigmine matrix layer or the self-adhesive matrix layer, or by adjusting the release controlling membrane, etc. Long-term stability is ensured even after controlling the release rate.

MODE FOR INVENTION

Hereinafter, the present disclosure is described in considerable detail with examples to help those skilled in the art understand the present disclosure. However, the following examples are offered by way of illustration and are not intended to limit the scope of the invention. It is apparent that various changes may be made without departing from the spirit and scope of the invention or sacrificing all its material advantages.

In the following comparative examples and examples, when expressed as simply "%" it means % by weight.

In the following comparative examples and examples, a PET film was used as a backing film, 3M's Scotchpak 9744 product was used as a release liner, and an ethylene vinyl acetate membrane, 3M CoTran™ 9707 was used as a release-controlling membrane.

In the following comparative examples and examples, unless otherwise stated, a self-adhesive polysiloxane polymer (Dow Corning® BIO-PSA, 1:1 mixture of 7-4201 and 7-4301) containing 0.1% of DL-alpha-tocopherol was used as a self-adhesive matrix layer.

Comparative Example 1 (4 Day Version of Exelon Patch

A patch consisting of (1) a backing film, (2) a self-adhesive matrix layer consisting of 30% by weight of rivastigmine, 20% by weight of plastoid B, 0.1% by weight of DL-alpha-tocopherol, and 49.9% by weight of a self-adhesive acrylic adhesive, (3) a self-adhesive matrix layer consisting of a self-adhesive polysiloxane polymer containing 0.1% by weight of DL-alpha-tocopherol, and (4) a release liner was prepared. It was prepared at 180 GSM (gram per square meter, $g/m^2$) based on the drug layer (rivastigmine content corresponds to 7.2 $mg/cm^2$; Exelon has 1.8 $mg/cm^2/day$ of rivastigmine content).

Comparative Example 2 (4 Day Version without Matrix Support Material

A patch with double-layer system consisting of (1) a backing film, (2) a self-adhesive matrix layer consisting of 40% rivastigmine, 0.1% DL-alpha-tocopherol, and 59.9% self-adhesive acrylic adhesive, (3) a self-adhesive matrix layer consisting of a self-adhesive polysiloxane polymer containing 0.1% DL-alpha-tocopherol, and (4) a release liner was prepared. It was prepared at 180 GSM based on the drug layer (rivastigmine content corresponds to 7.2 $mg/cm^2$).

Example 1

A patch with a triple layer system consisting of (1) a backing film, (2) a self-adhesive matrix layer consisting of 40% rivastigmine, 20% aerosil (AEROSIL® R 972 Pharma), 0.1% DL-alpha-tocopherol, and 39.9% self-adhesive acrylic adhesive (Duro-Tak® 87-235A), (3) a release-controlling membrane, (4) a self-adhesive matrix layer consisting of a self-adhesive polysiloxane polymer (Dow Corning® BIO-PSA, 1:1 mixture of 7-4201 and 7-4301) containing 0.1% DL-alpha-tocopherol, and (5) a release liner was prepared. It was prepared at 180 GSM based on the drug layer.

Example 2

A patch with a triple layer system consisting of (1) a backing film, (2) a self-adhesive matrix layer consisting of 30% rivastigmine, 15% aerosil (AEROSIL® R 972 Pharma), 0.1% DL-alpha-tocopherol, 5% Plastoid B, and 49.9% self-adhesive acrylic adhesive, (3) a release-controlling membrane, (4) a self-adhesive matrix layer consisting of a self-adhesive polysiloxane polymer containing 0.1% DL-alpha-tocopherol, and (5) a release liner was prepared. It was prepared at 180 GSM based on the drug layer.

Example 3

A patch with a triple layer system consisting of (1) a backing film, (2) a self-adhesive matrix layer consisting of 30% rivastigmine, 15% aerosil (AEROSIL® R 972 Pharma), 0.1% DL-alpha-tocopherol, 5% Eudragit L100, and 49.9% self-adhesive acrylic adhesive, (3) a release-controlling membrane, (4) a self-adhesive matrix layer consisting of a self-adhesive polysiloxane polymer containing 0.1% DL-alpha-tocopherol, and (5) a release liner was prepared. It was prepared at 180 GSM based on the drug layer.

Experimental Example 1 (Evaluation of Chemical Stability

Stability evaluation of rivastigmine was performed while storing the comparative examples and examples in a room temperature environment and an accelerated environment (40° C., 75% RH) in the following manner.

Ten round patches of 5 cm² size were placed in a 100 mL volumetric flask and diluted with an extraction solvent. After ultrasonic vibration for 60 minutes, 5 mL of this solution was taken at room temperature, put into a 10 mL volumetric flask, and evaporated for 30 minutes under a nitrogen stream. After putting the mobile phase, it was filtered through a 0.45 μm membrane filter.
Manufacturing of Mobile Phase
 2.02 g of 1-heptanesulfonate sodium was added to a 1 L volumetric flask, diluted with purified water, and adjusted to pH 3.0 with dilute phosphoric acid. Then, it was filtered through a 0.45 μm membrane filter.
Preparation of Extraction Solvent
 Methanol:ethyl acetate:triethylamine=70:30:0.4 (V/V/V)
HPLC Analysis Conditions
 Injection volume: 10 μL
 Column: RP18-C18, 250 mm×4.6 mm, 5 μm
 Detector: UV Detector (217 nm)
 Flow rate: 1.0 mL/min
 Run time: 30 minutes
 Mobile phase: 10 mM Sodium-1-heptane sulphonate buffer:acetonitrile (72:28).
The results are shown in Table 1 below.

TABLE 1

| Total Impurities | Accelerated Environment 1 month | Long Term 3 months | Long Term 6 months |
|---|---|---|---|
| Comparative example 1 | 0.41% | 0.24% | 0.35% |
| Comparative example 2 | 0.45% | 0.30% | 0.41% |
| Example 1 | 0.42% | 0.29% | 0.38% |
| Example 2 | 0.41% | 0.38% | 0.39% |
| Example 3 | 0.61% | 0.40% | 0.57% |

As shown in Table 1, the rivastigmine patch according to the present invention maintained its stability even if it contained a high amount of rivastigmine. When Eudragit L100 was additionally comprised in the rivastigmine matrix layer, the stability of rivastigmine was relatively inferior.

Experimental Example 2 (Evaluation of Physical Stability)

The following physical stability was measured.
Shear measurement method: After forming a 5 cm² circular patch, static shear was measured by connecting a 200 g weight.
Probe Tack measurement method: After forming a 1.7 cm² circular patch, the probe tack was measured.
Cold flow measurement method: 5 cm² circular patch was formed. After pressing with a 1 kg weight for 1 week, the cold flow (creep test) was measured. Alternatively, after leaving it open at 60-80° C. for 1 week, the cold flow was measured.
The results are shown in Table 2.

TABLE 2

| | Shear | Tack (g) | Cold flow (creep & heat test) |
|---|---|---|---|
| Comparative example 1 | Desorption within 24 hours | >200 g | Very severe |
| Comparative example 2 | Desorption within 1 hour | >200 g | Very severe |
| Example 1 | 72 hours or more | 100~150 g | Almost none |
| Example 2 | 72 hours or more | 100~150 g | Almost none |
| Example 3 | 72 hours or more | 100~150 g | Almost none |

As shown in the results of Table 2, the patch according to the present invention showed excellent physical stability.

Experimental Example 3 (Transdermal Penetration of Patch)

Figure 1:
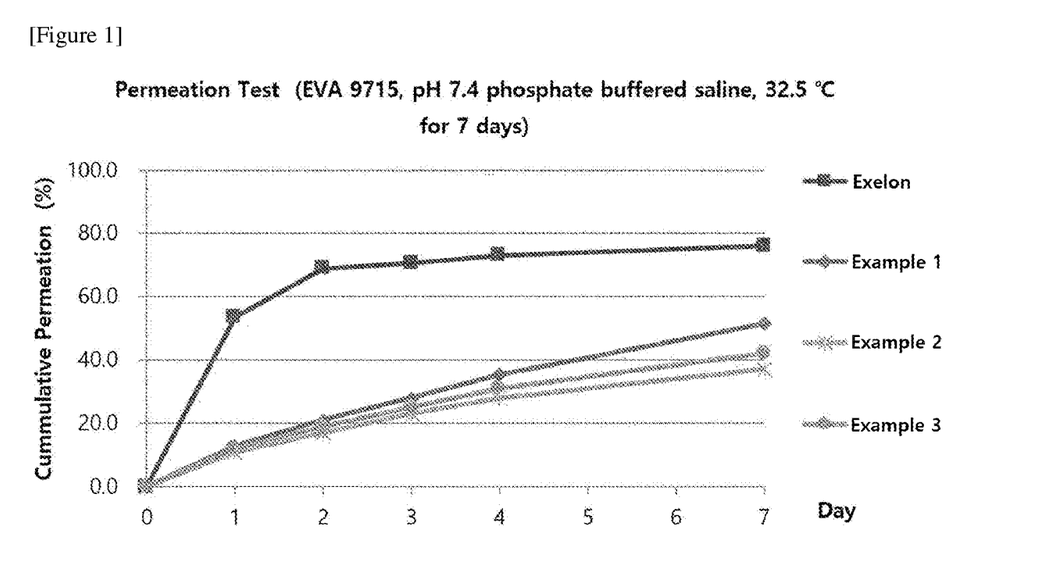
FIG. 1 is a graph showing the cumulative permeation percentages of examples of the present invention and a commercially available Exelon™ patch in a permeation test.
Figure 2:
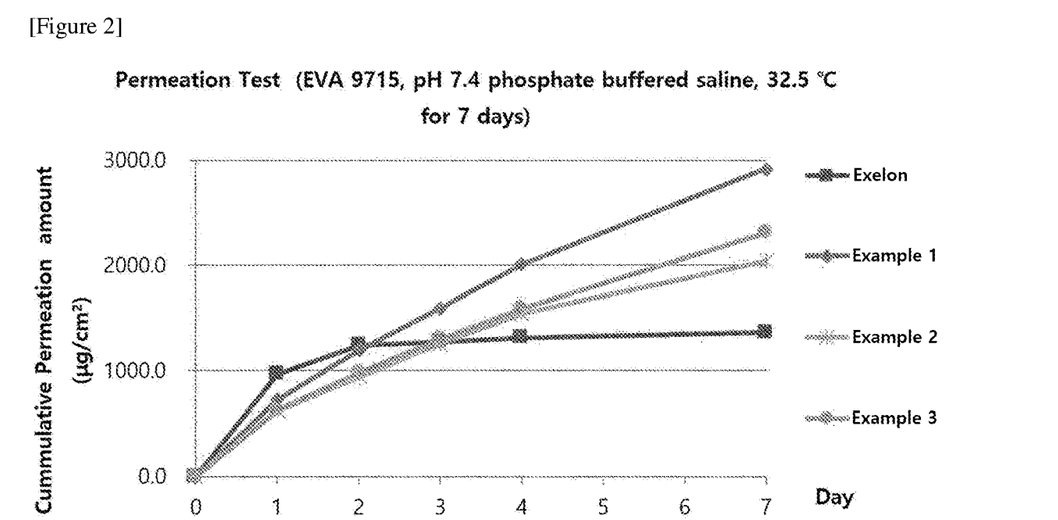
FIG. 2 is a graph showing the cumulative permeation amounts ($\mu g/cm^2$) of examples of the present invention and a commercially available Exelon™ patch in a permeation test.
Figure 3:
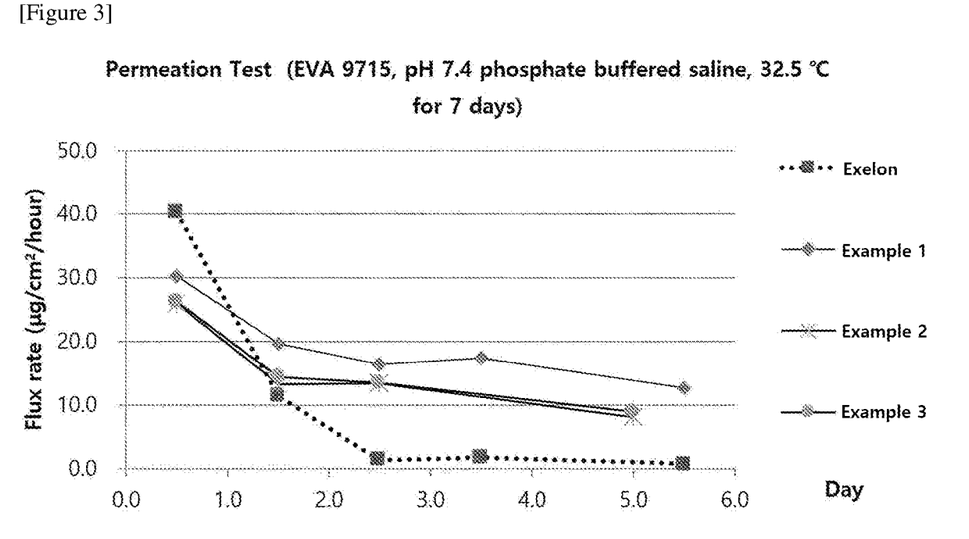
FIG. 3 is a graph showing changes in permeation rate ($\mu g/cm^2/hour$) of examples of the present invention and a commercially available Exelon™ patch in a permeation test.

Transdermal penetration experiments using a commercially available Exelon® patch were conducted under the following conditions.
Franz Diffusion Cell Experimental Parameters
 Apparatus: Hansen Automated Franz diffusion cell sampling system
 Cell volume: 7.0 mL
 Receptor solution: solution phosphate buffered saline (PBS, 1.0 M)
 Dose: 1.8 mg over a 1.0 cm2 area as rivastigmine base; occluded
 Duration: 7 days
 Temperature: 32.5° C.
 Sample volume: 0.9 mL
 Rinse volume: 1.6 mL
 Sample analysis: HPLC
 Membrane: 3M EVA 9715 membrane
The results are shown in Tables 3 to 5 and FIGS. 1 to 2.

TABLE 3

| | Flux rate at 1 day (μg/cm²/h) | Flux rate at 4 day (μg/cm²/h) | Decreasing rate of penetration from 24 hours to 96 hours (%) |
|---|---|---|---|
| Exelon ® patch | 25~30 μg | 0~5 μg | 80~90% |
| Examples 1~3 | 26~32 μg | 13~23 μg | Within 15~20% |

TABLE 4

| Day | Exelon ® patch | Example 1 | Example 2 | Example 3 |
|---|---|---|---|---|
| 0 | 0.0 | 0.0 | 0.0 | 0.0 |
| 1 | 53.6 | 12.8 | 11.0 | 12.0 |
| 2 | 68.9 | 21.1 | 17.0 | 19.0 |
| 3 | 70.6 | 28.0 | 23.0 | 25.0 |
| 4 | 72.9 | 35.3 | 28.0 | 31.0 |
| 7 | 76.0 | 51.4 | 37.0 | 42.0 |
| Content (mg/cm²) | 1.80 | 5.68 | 5.52 | 5.46 |

Table 4 shows the evaluation results of the cumulative penetration percentage (unit: %).

TABLE 5

| Day | Exelon ® patch | Example 1 | Example 2 | Example 3 |
|---|---|---|---|---|
| 1 | 965 | 725 | 620 | 630 |
| 2 | 1239 | 1198 | 940 | 980 |
| 3 | 1271 | 1592 | 1260 | 1300 |
| 4 | 1312 | 2007 | 1540 | 1590 |

TABLE 5-continued

| Day | Exelon ® patch | Example 1 | Example 2 | Example 3 |
|---|---|---|---|---|
| 7 | 1367 | 2919 | 2040 | 2310 |
| Content (mg/cm2) | 1.80 | 5.68 | 5.52 | 5.46 |

Table 5 shows the evaluation results of the cumulative penetration amount ($\mu g/cm^2$).

TABLE 6

| Day | Exelon ® patch | Example 1 | Example 2 | Example 3 |
|---|---|---|---|---|
| 0.5 | 40.2 | 30.2 | 25.9 | 26.3 |
| 1.5 | 11.4 | 19.7 | 13.3 | 14.4 |
| 2.5 | 1.3 | 16.4 | 13.4 | 13.5 |
| 3.5 | 1.7 | 17.3 | — | — |
| 4.5 | — | — | — | — |
| 5.0 | — | — | 8.1 | 8.9 |

TABLE 6-continued

| Day | Exelon ® patch | Example 1 | Example 2 | Example 3 |
|---|---|---|---|---|
| 5.5 | 0.8 | 12.7 | — | — |
| Content (mg/cm2) | 1.80 | 5.68 | 5.52 | 5.46 |

Table 6 shows the results of Flux rate ($\mu g/cm^2$/hour). From the experimental results obtained above, it was confirmed that the examples of the present invention can control the release of the drug continuously during the application period.

Experimental Example 4 (Evaluation of the Effect of Different Types of Silica)

Rivastigmine patches were prepared in the same manner as in Example 1, except that the components and contents of the rivastigmine matrix layer were prepared as shown in Table 7 below, and evaluated in substantially the same manner as in the experimental examples. The results are summarized and shown in Table 7 below.

TABLE 7

| Sample No. | Characteristics | API Content (mg/cm$^2$) | Probe Tack | Release peel | Shear (200 g, 5 cm$^2$) |
|---|---|---|---|---|---|
| Example a | 50% rivastigmine, 12% Aerosil A200P, Residual quantity of DT 235A | 10.0 | 160.0 ± 22.8 | Excellent | Inadequate |
| Example b | 44% rivastigmine, 22% Aerosil A200P, Residual quantity of DT 235A | 8.9 | 63.4 ± 7.2 | Excellent | N/A |
| Example c | 50% rivastigmine, 12% Aerosil A200P, Residual quantity of DT 235A | 9.3 | 154.2 ± 23.2 | Excellent | Excellent |
| Example d | 44% rivastigmine, 22% Aerosil A200P, Residual quantity of DT 235A | It was impossible to prepare. | | | |
| Example e | 50% rivastigmine, 12% Aerosil A300P, Residual quantity of DT 235A | 10.0 | 131.5 ± 11.2 | Inadequate | Excellent |
| Example f | 44% rivastigmine, 22% Aerosil A300P, Residual quantity of DT 235A | 8.9 | 35.4 ± 4.6 | Inadequate | N/A |
| Example g | 50% rivastigmine, 12% Aeroperl 300P, Residual quantity of DT 235A | 10.5 | 120.9 ± 27.3 | B/F and membrane separation phenomenon occurs | Inadequate |
| Example h | 44% rivastigmine, 22% Aeroperl 300P, Residual quantity of DT 235A | — | Cohesion Failure | It was difficult to prepare. | N/A |
| Example i | 44% rivastigmine, 22% Aerosil R972P, Residual quantity of DT 235A | 9.5 | 150.2 ± 19.4 | Release Peel Excellent | Excellent (kept >24 h) |

In Table 7, A200P means A 200 Pharma, A300P means A 300 Pharma, Aeroperl 300P means 300 Pharma, and R972P means R 972 Pharma. In Table 7, B/F means a backing film.

As shown in Table 7, when using Aerosil A200 and A300, the tap density was low, the properties were floppy, and it was difficult to use, and there was a problem in preparing the compositions for preparation of the patch. In the case of Aeroperl 300, it is easy to use because it has good solid properties, but when the amount is small, the tack improvement effect is small and cold flow is also severe. When the amount was increased, tack disappeared at all, and cohesion failure occurred at the level of loss of adhesion. In the case of Aerosil R972, it was easy to use due to its good solid properties. When using hydrophilic fumed silica, it is difficult to manufacture or product quality problems such as cold flow occurred.

Experimental Example 5 (Evaluation According to Rivastigmine Content)

According to Table 8 below, rivastigmine patches were prepared in a similar manner to Example 1. The following samples were prepared at 180 GSM based on the drug layer.

TABLE 8

| Item (Unit: wt %) | | 796-169-DT235A-RVS10 | 796-169-DT235A-RVS15 | 796-169-DT235A-RVS20 | 796-169-DT235A-RVS25 | 796-169-DT235A-RVS30 | 796-169-DT235A-RVS35 | 796-169-DT235A-RVS40 |
|---|---|---|---|---|---|---|---|---|
| Rivastigmine matrix layer | Rivastigmine (Content of rivastigmine per unit area $mg/cm^2$) | 10%<br>1.8 $mg/cm^2$ | 15%<br>2.7 $mg/cm^2$ | 20%<br>3.6 $mg/cm^2$ | 25%<br>4.5 $mg/cm^2$ | 30%<br>5.4 $mg/cm^2$ | 35%<br>6.3 $mg/cm^2$ | 40%<br>7.2 $mg/cm^2$ |
| | R972 | 20% | 20% | 20% | 20% | 20% | 20% | 20% |
| | DT235A (solids 40%) | 70% | 65% | 60% | 55% | 50% | 45% | 40% |
| | DL-Alpha-Tocopherol | 0.1% | 0.1% | 0.1% | 0.1% | 0.1% | 0.1% | 0.1% |
| Release controlling membrane | | 3M Cotran 9707 ||||||| 
| Self-adhesive matrix layer | BIO-PSA 7-4201 | 99.9% |||||||
| | DL-Alpha-Tocopherol | 0.1% |||||||

Figure 4:
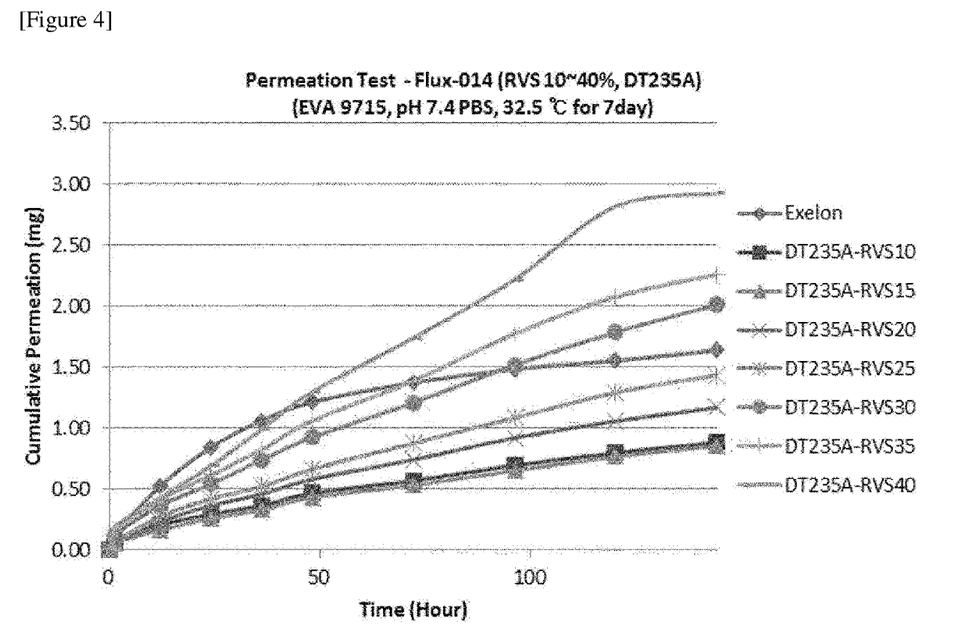
FIGS. 4 to 6 are graphs showing changes in cumulative permeation amount ($mg/cm^2$), cumulative permeation percentage (%), and permeation rate ($\mu g/cm^2/hour$), respectively, of examples for evaluating the effect of a change in content.
Figure 5:
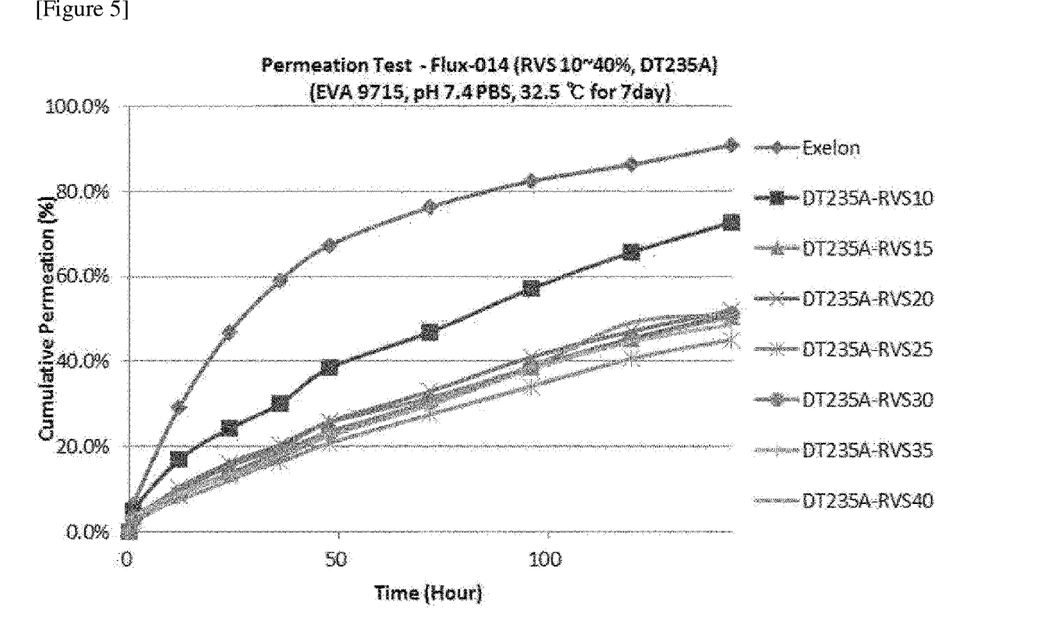
Figure 6:
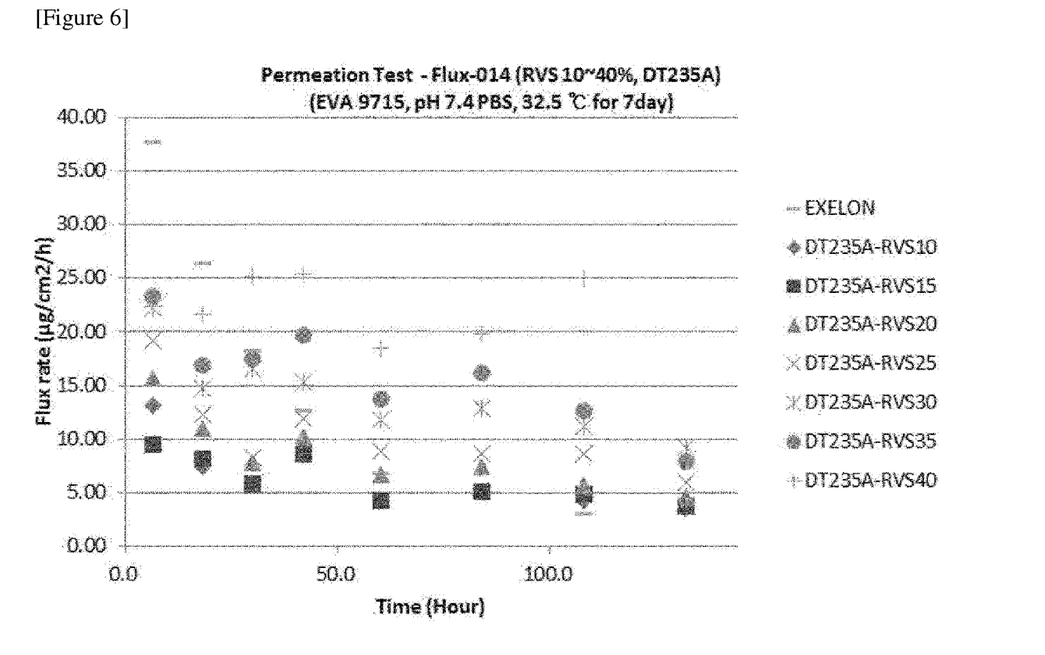

Thereafter, similar to Experimental Example 3, the transdermal permeation rate was measured for 7 days, and the results are shown in FIGS. 4 to 6. As shown in FIGS. 4 to 6, the rivastigmine patches according to the present invention could maintain a constant flux to some extent even after time.

Experimental Example 6 (Evaluation of Chemical Stability of Rivastigmine)

According to Table 9 below, rivastigmine patches were prepared in a similar manner to Example 1. The following samples were prepared at 180 GSM based on the drug layer.

TABLE 9

| Item | | 796-185-SK | 796-185-SK (No R972) |
|---|---|---|---|
| Rivastigmine matrix layer | Rivastigmine (Content of rivastigmine per unit area $mg/cm^2$) | 40%<br>7.2 $mg/cm^2$ | 40%<br>7.2 $mg/cm^2$ |
| | R972 | 20% | 0% |
| | DT235A (solids 40%) | 40% | 60% |
| | DL-Alpha-Tocopherol | 0.1% | 0.1% |

TABLE 9-continued

| Item | | 796-185-SK | 796-185-SK (No R972) |
|---|---|---|---|
| | Release controlling membrane | 3M Cotran 9707 ||
| Self-adhesive matrix layer | BIO-PSA 7-4201 | 99.9% ||
| | DL-Alpha-Tocopherol | 0.1% ||

The results of evaluating the degradation degree of rivastigmine after storing the samples prepared in Table 9 under severe conditions for 2 weeks are shown in Table 10 below.

TABLE 10

| | Patch (Accelerated condition, 60° C. 2 weeks) |||
|---|---|---|---|
| Sample ID | Single Max Impurity | Total Impurities | Purity at Final |
| 796-185_SK | 0.24% | 0.37% | 99.63% |
| 796-185_SK (NO R972) | 1.20% | 1.98% | 98.02% |

As shown in Table 10, when the hydrophobic silica is comprised according to the present invention, it was confirmed that the stability of rivastigmine was greatly helpful.

The invention claimed is:

1. A rivastigmine patch for transdermal treatment comprising a backing film; a rivastigmine matrix layer comprising rivastigmine; a self-adhesive matrix layer comprising an adhesive that adheres to the skin; and a release liner that is removed before use,
wherein the content per patch area of the rivastigmine is 5.4 to 15 mg/cm$^2$ based on the rivastigmine free base,
the rivastigmine matrix layer comprises a hydrophobic silica,
the self-adhesive matrix layer does not include a rubber-based adhesive polymer, and
the hydrophobic silica comprises silica dimethyl silylate.

2. The rivastigmine patch of claim 1, wherein the content per patch area of the rivastigmine is 5.4 to 10.8 mg/cm$^2$ based on the rivastigmine free base.

3. The rivastigmine patch of claim 2, wherein the content per patch area of the rivastigmine is 5.4 to 9 mg/cm$^2$ based on the rivastigmine free base.

4. The rivastigmine patch of claim 1, wherein the content of the hydrophobic silica is 10-50% by weight based on the total weight of the rivastigmine matrix layer.

5. The rivastigmine patch of claim 4, wherein the rivastigmine matrix layer comprises 10-50% by weight of the rivastigmine, 5-30% by weight of the hydrophobic silica, and 30-80% by weight of an acrylic adhesive based on the total weight of the rivastigmine matrix layer.

6. The rivastigmine patch of claim 5, wherein the acrylic adhesive is a random copolymer of 58-66 parts by weight of 2-ethylhexyl acrylate, 28-36 parts by weight of methyl acrylate, and 4-8 parts by weight of acrylic acid.

7. The rivastigmine patch of claim 4, wherein the content per patch area of the rivastigmine is 5.4 to 10.8 mg/cm$^2$ based on the rivastigmine free base.

8. The rivastigmine patch of claim 4, wherein the content per patch area of the rivastigmine is 5.4 to 9 mg/cm$^2$ based on the rivastigmine free base.

9. The rivastigmine patch of claim 1, wherein the rivastigmine matrix layer further comprises an antioxidant.

10. The rivastigmine patch of claim 1, wherein the rivastigmine patch comprises a release-controlling membrane that is an ethylene vinyl acetate film between the rivastigmine matrix layer and the self-adhesive matrix layer.

11. The rivastigmine patch of claim 1, wherein the self-adhesive matrix layer comprises a mixture of two or more silicone adhesives having different physical properties.

12. The rivastigmine patch of claim 1, wherein the rivastigmine patch is capable of continuous release of rivastigmine for at least 3 days after attachment.

* * * * *